United States Patent [19]
Mann et al.

[11] Patent Number: 5,719,194
[45] Date of Patent: Feb. 17, 1998

[54] PREVENTION AND TREATMENT OF TOPICAL VIRAL INFECTIONS WITH PERFLUOROPOLYETHERS OR COMPOSITIONS THEREOF

[75] Inventors: Morris A. Mann, Phoenix, Ariz.; Giovanni Pantini, Milano, Italy

[73] Assignee: Ausimont S.p.A., Milan, Italy

[21] Appl. No.: 663,022

[22] Filed: Jun. 7, 1996

[30] Foreign Application Priority Data

May 28, 1996 [IT] Italy ............................. 96A001070

[51] Int. Cl.$^6$ ........................... A01N 31/02; C07C 43/12
[52] U.S. Cl. .............. 514/723; 424/405; 424/78.02; 424/78.07; 424/78.38; 568/601; 568/602; 568/604; 568/615
[58] Field of Search ................ 514/723; 568/601, 568/602, 604, 615; 424/405, 78.02, 78.07, 78.38

[56] References Cited

U.S. PATENT DOCUMENTS

| | | | |
|---|---|---|---|
| 3,897,502 | 7/1975 | Russel et al. | 260/614 F |
| 5,368,847 | 11/1994 | Brunetta et al. | 424/61 |

FOREIGN PATENT DOCUMENTS

| | | |
|---|---|---|
| 0 196 904 A2 | 10/1986 | European Pat. Off. . |
| 0 250 766 A1 | 1/1988 | European Pat. Off. . |
| 0 390 206 A2 | 10/1990 | European Pat. Off. . |
| 0 494 412 A2 | 7/1992 | European Pat. Off. . |

OTHER PUBLICATIONS

European Search Report. EP 96 11 1163. Jul. 28, 1997.

*Primary Examiner*—Peter O'Sullivan
*Attorney, Agent, or Firm*—Watson Cole Stevens Davis, P.L.L.C.

[57] ABSTRACT

Use of perfluoropolyethers with non reactive terminals or compositions thereof for the prevention and/or the treatment of topical viral infections, in particular of Herpes Simplex I and II and of Herpes Zoster.

10 Claims, No Drawings

PREVENTION AND TREATMENT OF TOPICAL VIRAL INFECTIONS WITH PERFLUOROPOLYETHERS OR COMPOSITIONS THEREOF

This application claims to benefit of U.S. Provisional application Ser. No. 60/002,665, filed 22 Aug. 1995.

The present invention relates to the use of perfluoropolyethers and compositions thereof for preventing and/or treating topical viral infections.

It is well known that the way in which viruses are able to infect living cells is not entirely understood. However, it is known that viruses are capable of infecting cells through fusion and endocytosis. Some viruses, such as herpes, pox, and paramyxo-paramyxyl viruses are agents whose outer envelope is composed of a lipid bilayer in which viral glycoproteins are imbedded. These viruses appear to enter living cells by fusion of the envelope with the host cell plasma membrane. In other types of viruses, such as myxo, toga, rhabdo, and oncorna viruses, infection occurs as a result of the virus being engulfed by the host cell in a phagocytic vacuole. In other viruses such as oncorna, but also reo, papova, and adeno viruses, an additional uncoating stem will occur within the cytoplasm.

It has been postulated that infection is related to protein-protein interaction consisting of an electrostatic bonding. In other words, if the cell membrane has a negative charge, one can deduce that the viral capsid protein has a positive charge. This will result in an attraction of the virus to the cell membrane with consequent infection and reproduction of the virus within the cell itself.

The ability to block viral reproduction and infection topically is an extremely important objective.

It is well known that topical viral infections are rampant in western society. These include Herpes Simplex Types I and II, the various viruses that produce genital warts; i.e., papova viruses, and others.

It would be highly desirable to have a compound or a composition that would prevent infections by these agents or that could be effectively used for treating topical infections caused by these viral agents.

The Applicant has unexpectedly and surprisingly found that the use of a perfluoropolyether with non-reactive terminals, or compositions containing said compound, results effective for preventing and/or treating topical viral infections, in particular Herpes Simplex I and II and Herpes Zoster.

The treatment with the compounds of the present invention is carried out by local applications in the affected area. It has been surprisingly found by the Applicant that the above mentioned viral topical infections, in particular the aforesaid types of Herpes, treated in this way, do not show recurrent phenomena in persons particularly predisposed to recurrences. In this case it is sufficient a repeated treatment with the compounds of the invention for preventing recurrences as indicated above.

Moreover, no side effects have been noted with the use of the compounds of the invention, in particular no irritating and sensitizing side effects have been noticed.

Although not intending to be bound by any theory on the action mechanisms of the compounds of the present invention, it is believed that perfluoropolyethers block the ability of herpes virus and other viruses to return to the nerve root. So it is avoided that the virus returns in its latent phase thus maintaining the potential to infect living cells. The topical treatment with perfluoropolyethers in substance seems to eliminate the latent phase and therefore the possibility of recurrences. To date, no other treatment has demonstrated this result, i.e. the elimination of recurrences.

In the context of this invention, the following terms will be defined as follows unless otherwise stated. The terms "infect, infected, infection" as they are used broadly herein, mean penetration of a living cell by a viral protein capable of replication. The term "living cell" as used broadly herein, refers to cells containing a nucleus that would have the potential for replication.

The amount of the utilized perfluoropolyether is the minimum one capable of covering a topical lesion. Amounts from 0.1–200 ml can generally be utilized. Higher amounts could be necessary in the case of a diffuse topical viral infection. The perfluoropolyethers utilized in the present invention are inert liquid compounds well known in the art. They comprise repeating units statistically distributed along the chain of the polymer, selected from: $-CF_2CF_2O-$, $-CFXO-$ wherein X is equal to F or $CF_3$, $-C_3F_6O-$, $-CF_2(CF_2)_zO-$ wherein z is an integer equal to 2 or 3, $-CF_2CF(OR_f)O-$, $-CF(OR_f)O-$ wherein $R_f$ is equal to $-CF_3$, $-C_2F_5$, $-C_3F_7$.

The perfluoropolyethers terminals are, as already said, inert and can be $-CF_3$, $-C_2F_5$, $-C_3F_7$, $ClCF_2CF(CF_3)-$, $CF_3CFClCF_2-$, $ClCF_2CF_2-$, $ClCF_2-$. The perfluoroalkylic terminals are preferred.

The number average molecular weight of the perfluoropolyethers of this invention is generally higher than 500 and typically ranges from 1,000 to 10,000, preferably from 3,000 to 8,000.

The following perfluoropolyethers can be particularly mentioned:

(a) $-O(CF_2CF(CF_3)O)_a(CFXO)_b-$ wherein X is F or $CF_3$; a and b are such integers that the molecular weight is comprised in the range indicated above; a/b is comprised between 10 and 100, (b) $-O(CF_2CF_2O)_c(CF_2O)_d(CF_2(CF_2)_zCF_2O)_h-$ wherein c, d and h are such integers that the molecular weight is comprised in the range indicated above; c/d is comprised between 0.1 and 10; h/(c+d) is comprised between 0 and 0.05, z has the above indicated value, (c) $-O(CF_2CF(CF_3)O)_e(CF_2CF_2O)_f(CFXO)_g-$ wherein X is F or $CF_3$; e, f, g are such numbers that the molecular weight is comprised in the range indicated above; e/(f+g) is comprised between 0.1 and 10, f/g is comprised between 2 and 10, (d) $-O(CF_2O)_j(CF_2CF(OR_f)O)_k(CF(OR_f)O)_l-$ wherein: $R_f$ is $-CF_3$, $-C_2F_5$, $-C_3F_7$; j,k,l are such numbers that the molecular weight is comprised in the range indicated above; k+l and j+k+l are at least equal to 2, k/(j+l) is comprised between 0.01 and 1000, l/j is comprised between 0.01 and 100, (e) $-(CF_2(CF_2)_zCF_2O)_s-$ wherein s is such an integer as to give the molecular weight indicated above, z has the meaning already defined.

These compounds and the methods for preparing them are described in patents GB 1,104,482, U.S. Pat. No. 3,242,218, U.S. Pat. No. 3,665,041, U.S. Pat. Nos. 3,715,378 and 3,665,041, EP 148,482 and U.S. Pat. No. 4,523,039.

The preferred perfluoropolyethers of the present invention have the following chemical structure:

wherein the n/m ratio ranges from about 20 to about 40.

These compounds are produced by Ausimont, Milano, Italia and commercialized with the tradename "Fomblin HC". Said compounds are described in U.S. Pat. Nos. 4,803,067; 4,959,171 and 5,093,023. Commercial examples of said compounds Fomblin HC comprise Fomblin HC/04 (number average molecular weight 1500), Fomblin HC/25 (number average molecular weight 3200), and Fomblin HC/R (number average molecular weight 6250).

The properties of these compounds are reported in Table 1.

TABLE 1

FOMBLIN HC properties

| Properties (typical values) | HC/04 | HC/25 | HC/R |
|---|---|---|---|
| Average molecular weight | 1500 | 3200 | 6250 |
| Kinematic viscosity at 20° C. (cSt) | 40 | 250 | 1300 |
| Pour value (°C.) | −62 | −35 | −25 |
| Vapor tension (mm Hg) | $10^{-3}$ | $10^{-5}$ | $10^{-7}$ |
| Evaporation loss 1 h at 105° C. (g/100 g) | 0.5 max | 0.05 max | 0.02 max |
| Neutralization No. (mg KOH/g) | 0.02 max | 0.02 max | 0.02 max |
| Interfacial tension against water at 20° C. (dine/cm) | 55 min | 55 min | 55 min |
| Surface tension at 20° C. (dine/cm) | 21 | 22 | 24 |
| Refractive index | 1.293 | 1.299 | 1.302 |
| Density (g/cm$^3$) | 1.87 | 1.90 | 1.91 |

The solubility of Fomblin HC indicated above in various solvents is reported in Table 2.

TABLE 2

Solubility of FOMBLIN HC in various solvents

| Solvent | HC/04 | HC/25 | HC/R |
|---|---|---|---|
| Water | I | I | I |
| Ethanol | I | I | I |
| Glycerin | I/D | I/D | I/D |
| Glycerin (plus 5% water) | I/D | I/D | I/D |
| Diglycerine | I/E | I/D | I/D |
| Acetone | I | I | I |
| Polyethylene glycol | I | I | I |
| Sorbeth-30 | I | I | I |
| Glyceryl Mono Distearate | I | I | I |
| Caprylic/Capric Triglyceride | I | I | I |
| Sodium lauryl ether sulphate | I | I | I |
| Mineral oil | I | I | I |
| Dimethicone | I | I | I |
| HCFC-124 | S | S | S |
| HFC-134a | S | S | — |
| Trichloro-trifluoroethane | M | M | M |
| Perfluoro-octane | M | M | M |

I = insoluble (less than 10 ppm soluble)
D = dispersible
S = soluble (more than 10% by weight soluble)
M = miscible.

As already said perfluoropolyethers can also be utilized according to the present invention in compositions containing them.

The perfluoropolyether compositions for treating topical viral infection, in particular the various kinds of herpes (Herpes Simplex I and II, Herpes Zoster) must be such as to assure a high concentration and persistence of the perfluoropolyether in the zone to be treated. The amount of perfluoropolyether to this end must be of the order of magnitude indicated above for the pure compound. Moreover, the compositions must be sufficiently agreeable preparations, without causing irritations or sensitizations, and meeting the rule system of the various countries for cosmetics. Therefore raw materials of common cosmetic/dermatologic use are to be employed, which result therefore excipients in the case of registration of preparations as pharmaceutical products, and as such without physiologic activity (inert). The preparations will have to be of different viscosity and presentation depending on the herpes type: with HSV I (Herpes Simplex I) it will be necessary a labial treatment, with HSV II (Herpes Simolex II) it will be necessary a treatment of genitals and with Herpes Zoster (St. Anthony's fire) a treatment will be necessary on a broader body surface.

In order to assure a higher persistence it is in general preferable to have anhydrous systems. For these reasons, in particular as regards persistence, a perfluoropolyether made more viscous with a thickener, preferably micronized PTFE, can be considered the best solution.

In general it is possible to have three groups of preparations:

1) perfluoropolyethers/glycerine emulsions (or other polyhydroxylates).
2) perfluoropolyethers preferably thickened with micronized silica, or alternatively, with alumina or modified clays. The amount of these modifiers generally ranges between 0.1 and 4% by weight, preferably between 0.2 and 2% by weight. The size of these modifiers is the one reported in point 3) hereinafter.
3) perfluoropolyether pastes with PTFE or inorganic compounds such as zinc oxide, titanium dioxide, boron azide. The amount of these thickening compounds ranges between 4 and 45% by weight, preferably between 20 and 40% by weight. Said thickeners generally have average particle sizes comprised between 3 and 10 micron, preferably between 5 and 8 micron.

Perfluoropolyether emulsions with glycerin

These dispersions are described in European patent EP 390,206 and in the articles "Emulsioni anidre di perfluoropolieteri", Brunetta F., Guidolin V., Pantini G., Cosmetic & Toiletries (Italian edition 2/92) and "Perfluoropolyethers: Status and New Developments", Pantini G., Brunetta F., Guidolin V., Cosmetic & Toiletries (10) 71 "Allured Publishing Corp., (International edition), October 1991. See also "Multiple Emulsions comprising a Perfluoropolyether (Fomblin HC), Brunetta F., Pantini G., Soefw Journal, Cosmetics Detergents Specialities, 1. September-heft 1993, 11.

Briefly, said emulsions are obtained by addition of perfluoropolyether, under strong stirring, for example by using Silverson L2R mixer for 5/10 minutes, followed by slower stirring for further 30 minutes at room temperature, in anydrous glycerin (>98% by weight), wherein a surfactant, preferably ionic, has been dissolved in concentration between 0.2–2% by weight. The perfluoropolyether must have a concentration higher than 1% by weight, preferably >30% by weight, and preferably have a high viscosity (Fomblin HC/R). In order to obtain the desired viscosity, the use of a rheologic auxiliary product, such as acrylic compounds (Carbomer, for instance Carbopol manufatured by B F Goodrich), can be of help.

Examples of emulsion are the following (% by weight)
Fomblin HC/R 30.00%
Glycerin 69.00%
Sodium lauryl ether sulphate 1.00%
or
Fomblin HC/R 30.00%
Nonylphenolethoxylate-9 (9-EO) 30.00%
Sodium lauryl ether sulphate 0.25%
Glycerin 39.75%

The perfluoropolyether/glycerin emulsions appear as very white, viscous and slightly sticky preparations.

Perfluoropolyethers thickened with silica

By using micronized silica ("smoked silica", Aerosil 200 or Aerosil 300, Degussa AG), it can be obtained gelled systems, but still fluid, till real solid gels, by operating with additions from 0.2% up to 4% (the remainder is perfluoropolyether). The silica is gradually added under stirring (Silverson L2R) to perfluoropolyether at room temperature, it is stirred then for further 5 minutes with increase of the temperature (because of the mechanical action one arrives at 60° C.), stirring is continued up to cooling.

Examples of preparations can be the following:
Fomblin HC/R 99.00%
Aerosil 200 1.00%
Viscosity: 18,600 mPas
or
Fomblin HC (having number average 99.50%
molecular weight of about 7000)
Aerosil 200 0.50%
Viscosity 15,000 mPas
or
Fomblin HC/04 98.00%
Aerosil 200 2.00%
Viscosity 63,000 mPas A clay can be used instead of the silica. An example is reported:
Fomblin HC/R 97.00%
Bentone gel SVS 3.00%

The silica could be replaced also by alumina.

Pastes with PTFE or pigments

The use of micronized PTFE (with gamma radiations) allows to obtain pefluoropolyether white pastes sticking to the skin in a very persistent way.

The most notable example regards a preparation of Ausimont (commercial name: Fomblin HC/P-R) consisting of:
Fomblin HC/R 70%
Algoflon HC 30%

The preparation is obtained by gradually adding under stirring Algoflon to Fomblin HC/R, it is let stand a night, then one proceeds to stirring and homogenization for some hours. Algoflon HC is a white powder, with average particles in the 5–7 micron range.

Pigments or inorganic powders as boron azide, zinc oxide or the titanium dioxide, in concentrations preferably higher than 10%, and generally in the 20–40% range, could be employed instead of the micronized PTFE. White pastes are obtained.

As an example, a preparation obtained from boron azide by Advanced Ceramics (USA) is reported herein:
Fomblin HC/R 80.00%
Boron azide AD BN Powder $CC_{6004}$ 20.00%

A very white, very viscous and covering paste, when applied to the skin, is obtained.

As already said, the amount of perfluoropolyether for topical lesions will vary depending on the infection extension. The typical administering method resides in covering the affected part with perfluoropolyether or a perfluoropolyether composition every three-four hours. A systemic infection with Herpes Zoster may require application of substantially a greater amount of perfluoropolyether or perfluoropolyether composition than a simple oral Herpes Simplex Type I lesion.

The following examples detailing a treatment modality with the perfluoropolyethers of the invention are illustrative only and should not be construed as limiting the invention in any way. The examples have been carried out for preventing and treating Herpes Types I and II lesions which were considered ideal for the following study because of their inherent cyclicity. Other topical viral infections can however be treated according to the present invention.

EXAMPLE I

Ten patients with Herpes Simplex Type I lesions primarily affecting the oral and nasal area were treated over a period of five months. These individuals were specifically selected because of the rapid cyclicity of their infections. They had outbreaks on the average of once every two or three weeks. They were given Fomblin HC/R and instructed to apply it to the affected areas every three to four hours whenever a viral lesion occurred. In all cases, clearing occured within 72 hours and all lesions had disappeared within five days. Of these ten patients, only one patient experienced a recurrence; and this recurrence was limited to a single lesion which disappeared within three day and never recurred.

EXAMPLE II

A second group of ten patients was selected, all of whom suffered from Herpes Progenitalis Type II. Once again, these individuals were selected because of the rapid cyclicity of their infections. All of them had a history of recurring lesions every two to four weeks. As with the previous group, they were instructed to apply the Fomblin HC/R to the affected areas every three to four hours when viral lesions appeared. In all cases, clearing occurred within 72 hours and lesions disappeared within five days from the initiation of treatment. There were no recurrences.

EXAMPLE III

Two cases of obvious Herpes Zoster were seen over thoracia lesions. These patients were also instructed to apply Fomblin HC/R to the affected area every three to four hours. Surprisingly, in both cases, the lesions healed completely in less than a week, and there was no sensitivity or pain in the previously affected area as would normally be the case with a healed infection due to Herpes Zoster.

There was no evidence of allergic reaction, irritation, or delayed sensitivity associated with the use of the perfluoropolyether, Fomblin HC/R.

The present invention may, of course, be carried out in other specific ways than those herein set forth, without departing from the spirit and essential characteristics of the invention. The present embodiments are, therefore, to be considered in all respects as illustrative and not restrictive and all changes come within the scope of the invention.

We claim:

1. A method for preventing and/or treating topical viral infections by locally applying thereto perfluoropolyethers with non-reactive terminals or compositions containing said perfluoropolyethers.

2. The method of claim 1, wherein the amount of perfluoropolyether utilized is the minimal one capable of covering a topical lesion.

3. The method of claim 2, wherein the amount of perfluoropolyether is comprised between 0.1–200 ml.

4. The method of claim 1, wherein the perfluoropolyethers comprise repeating units statistically distributed along the chain of the polymer, selected from: —$CF_2CF_2O$—, —CFXO— wherein X is equal to F or $CF_3$, —$C_3F_6O$—, —$CF_2(CF_2)_zO$— wherein z is an integer equal to 2 or 3, —$CF_2CF(OR_f)O$—, —$CF(OR_f)O$— wherein $R_f$ is equal to —$CF_3$, —$C_2F_5$, —$C_3F_7$.

5. The method of claim 4, wherein the perfluoropolyethers terminals are —$CF_3$, —$C_2F_5$, —$C_3F_7$, $ClCF_2CF(CF_3)$—, $CF_3CFClCF_2$—, $ClCF_2CF_2$—, $ClCF_2$—.

6. The method of claim 1, wherein the number average molecular weight of the perfluoropolyether is higher than 500.

7. The method of claim 6, wherein the number average molecular weight of the perfluoropolyether is comprised between 3,000 and 8,000.

8. The method of claim 4, wherein the perfluoropolyethers are selected from:

(a) —$O(CF_2CF(CF_3)O)_a(CFXO)_b$— wherein X is F or $CF_3$; a and b are such integers that the molecular weight is comprised in the range indicated above; a/b is comprised between 10 and 100, (b) —$O(CF_2CF_2O)_c(CF_2O)_d(CF_2(CF_2)_zCF_2O)_h$— wherein c, d and h are such integers that the molecular weight is comprised in the range indicated above; c/d is comprised between 0.1 and 10; h/(c+d) is comprised between 0 and 0.05, z has the above indicated value, (c) —$O(CF_2CF(CF_3)O)_e(CF_2CF_2O)_f(CFXO)_g$— wherein X is F or $CF_3$; e, f, g are such numbers that the molecular weight is comprised in the range indicated above; e/(f+g) is comprised between 0.1 and 10, f/g is comprised between 2 and 10, (d) —$O(CF_2O)_j(CF_2CF(OR_f)O)_k(CF(OR_f)O)_m$— wherein: $R_f$ is —$CF_3$, —$C_2F_5$, —$C_3F_7$; j,k,l are such numbers that the molecular weight is comprised in the range indicated above; k+l and j+k+l are at least equal to 2, k/(j+l) is comprised between 0.01 and 1000, l/j is comprised between 0.01 and 100, (e) —$(CF_2(CF_2)_zCF_2O)_s$— wherein s is such an integer as to give the molecular weight indicated above, z has the meaning already defined.

9. The method of claim 8, wherein the pefluoropolyether has the formula

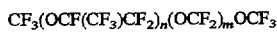

$$CF_3(OCF(CF_3)CF_2)_n(OCF_2)_mOCF_3$$

wherein the n/m ratio ranges from about 20 to about 40.

10. The method of claim 1 wherein the perfluoropolyether or composition containing same is applied to Herpes Simplex I, II and, Herpes Zoster.

* * * * *

UNITED STATES PATENT AND TRADEMARK OFFICE
CERTIFICATE OF CORRECTION

PATENT NO. : 5,719,194

DATED : February 17, 1998

INVENTOR(S) :
Mann et al.

It is certified that error appears in the above-identified patent and that said Letters Patent is hereby corrected as shown below:

ON THE TITLE PAGE ,

Item [73], first Assignee, insert therefor -- Morris A. Mann, Phoenix, Ariz.; --

ON THE TITLE PAGE, INSERT THE FOLLOWING:
--[60] PROVISIONAL APPLICATION 60/002,665, AUGUST 22, 1995

Signed and Sealed this

Eighteenth Day of May, 1999

Attest:

Q. TODD DICKINSON

*Attesting Officer*     *Acting Commissioner of Patents and Trademarks*